(12) United States Patent
Harmer et al.

(10) Patent No.: US 7,897,807 B2
(45) Date of Patent: *Mar. 1, 2011

(54) MANUFACTURE OF HYDROFLUOROALKANESULFONIC ACIDS

(75) Inventors: Mark Andrew Harmer, Landenberg, PA (US); Christopher P. Junk, Wilmington, DE (US); Zoe Schnepp, Beech Hill (GB)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/709,531

(22) Filed: Feb. 22, 2010

(65) Prior Publication Data

US 2010/0145093 A1 Jun. 10, 2010

Related U.S. Application Data

(62) Division of application No. 11/447,713, filed on Jun. 6, 2006, now Pat. No. 7,683,209.

(60) Provisional application No. 60/688,263, filed on Jun. 7, 2005.

(51) Int. Cl.
*C07C 309/04* (2006.01)
*C07C 309/19* (2006.01)

(52) U.S. Cl. ............... 562/113; 562/111; 562/116; 562/123

(58) Field of Classification Search .......... 562/111, 562/123, 113, 116
See application file for complete search history.

(56) References Cited

U.S. PATENT DOCUMENTS 2,403,207 A 7/1946 Barrick
2007/0019708 A1* 1/2007 Shiflett et al. ............... 374/181

FOREIGN PATENT DOCUMENTS

| CN | 1097191 A | 1/1995 |
| JP | 9104686 A | 4/1997 |
| WO | 2006084262 A1 | 8/2006 |

OTHER PUBLICATIONS

Kilian, A. and Waeschke, H.; "Synthesis of 1,1,2,2-Tetrafluoroethane Sulfonic Acid (TFESA) in the Autoclave", Wissenschaftliche Beitrage, Ingenieurhochschule Kothen, pp. 22-28 (1978).
Koshar, R. J. et al; "Preparation of Beta-H-Perfluoro Alkanesulphonic Acids", Journal of the American Chemical Society, vol. 75, No. 18, Sep. 20, 1953, pp. 4595-4596, American Chemical Society, Washington, DC.

* cited by examiner

*Primary Examiner*—Peter G O'Sullivan

(57) ABSTRACT

A process for manufacture of hydrofluoroalkanesulfonic acid with at least one hydrogen bonded to the carbon atom adjacent to the carbon atom bonded to the sulfonic acid group comprising: contacting a fluoroolefin with sulfite in an aqueous solution adjusted to about pH 4 to pH 12; removing water from the solution to form a solid; directly treating the solid with oleum; and distilling the hydrofluoroalkanesulfonic acid therefrom. Also a process for manufacture of potassium hydrofluoroalkanesulfonate in high purity is described.

2 Claims, No Drawings

MANUFACTURE OF HYDROFLUOROALKANESULFONIC ACIDS

BACKGROUND OF THE INVENTION

1. Field of the Invention

This invention is in the field of strong acids useful for catalysis.

2. Description of Related Art

Trifluoromethanesulfonic acid is used for catalysis where a strong acid is needed. It offers a safer, more easily handled alternative to the inorganic acids, hydrogen fluoride and sulfuric acid, which are widely used in industrial processes. Known hydrofluoroalkanesulfonic acids, such as tetrafluoroethanesulfonic acid (TFESA), could be more effective candidates to replace trifluoromethanesulfonic acid in catalytic applications.

Hydrofluoroalkanesulfonic acids are made by the addition of the elements of sulfurous acid, $H_2SO_3$, to fluoroolefins. For example, TFESA is the product of the reaction with tetrafluoroethylene (TFE):

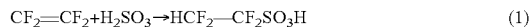

$$CF_2=CF_2+H_2SO_3 \rightarrow HCF_2-CF_2SO_3H \qquad (1)$$

In practice, the fluoroolefin is reacted with aqueous sulfite solution, usually an alkali metal sulfite. The solution is buffered to suppress the competing reaction, hydration of the fluoroolefin to form a carboxylic acid byproduct. In the case of TFE, the acid resulting from hydration is difluoroacetic acid, $HCF_2CO_2H$.

The literature does not provide an efficient manufacturing method for this reaction. An early reference, U.S. Pat. No. 2,403,207 (1946), teaches the optional use of free radical initiator. A. Kilian and H. Waeschke in Wissenschäftliche Beiträge, Ingenieurhochschule Köthen, pp. 22-28 (1978), teach the utility of peroxide initiator for the reaction. Borax is generally used as the buffer. Extraction, usually with ethanol, is used to recover the product salt or acid. Typically, the reaction mixture is worked up by drying, followed by extraction with hot ethanol. The extract is dried to remove the ethanol and the resulting solid is treated with sulfuric acid. This mixture is distilled to yield the hydrofluoroalkanesulfonic acid, usually as a hydrate if any water is present, and byproduct organic acid or acetate. If the unhydrated hydrofluoroalkanesulfonic acid is needed, a further step, such as treatment with thionyl chloride, is necessary. As late as 1995, Chinese Patent Application 1097191 noted the shortcomings of the available manufacturing methods ("harsh reaction conditions, low yield, low reaction uniformity and high cost") and proposed replacement of water with aqueous organic solutions and the use of organic ammonium compounds in the reaction. These proposed modifications make the reaction more complex and expensive. Two years later and fifty years after the '207 patent, Japanese Patent Application 9-104686 (1997) disclosed preparative examples of the reactions with TFE and with hexafluoropropylene (HFP) with aqueous sulfite. Reaction times were 110 hours and yields 20% or less.

A simplified process is needed for making hydrofluoroalkanesulfonic acids in good purity and yield.

BRIEF SUMMARY OF THE INVENTION

The present invention provides a process for manufacture of hydrofluoroalkanesulfonic acid with at least one hydrogen bonded to the carbon atom adjacent to the carbon atom bonded to the sulfonic acid group comprising, a) contacting a fluoroolefin with sulfite in an aqueous solution adjusted to about pH 4 to pH 12; b) removing water from the solution to form a solid; c) directly treating the solid with oleum to form a mixture that includes hydrofluoroalkanesulfonic acid; and d) distilling the hydrofluoroalkanesulfonic acid from the mixture. The process simplifies the recovery of the final product since extractive steps and the attendant solvents can be eliminated.

Preferred processes according to this invention eliminate the use of initiators as being deleterious to the desired addition reaction, and/or buffer the reaction without introducing extraneous reagents such as borax or phosphate, promoting rapid reaction with little or no byproduct, and without contamination of the final product (hydrofluoroalkanesulfonic acid) by buffer-derived impurities.

The present invention further provides a process for manufacture of potassium hydrofluoroalkanesulfonate with at least one hydrogen bonded to a carbon atom adjacent to the carbon atom bonded to the sulfonate group comprising: a) contacting fluoroolefin having at least three carbon atoms with an aqueous solution of sulfite and counter ion in which the counter ion comprises potassium, said solution having a pH of about 4 to 12; and b) employing conditions which cause potassium hydrofluoroalkanesulfonate to precipitate from said solution.

The present invention also provides potassium salts of $R_f$—CFH—$CF_2SO_3^-$ wherein $R_f$ is selected from the group consisting of fluoroalkyl groups, perfluoroalkyl groups, cyclofluoroalkyl groups and cycloperfluoroalkyl groups, said groups optionally containing ether oxygen.

DETAILED DESCRIPTION OF THE INVENTION

Fluoroolefins employed according to this invention are olefins having at least one fluorine atom bonded to a doubly-bonded carbon. Preferably, the fluoroolefin has a terminal double bond, i.e. has a vinyl group. One class of fluoroolefins of this type has the formula: a) if acyclic, $C_nF_aH_bX_c$ where X is a halogen, $a \geq 1$, b=0 to 2n-1, and c=0 to 2n-1, and a+b+c=2n, at least one F being bonded to a doubly bonded carbon atom, preferably being a vinyl F, that is a fluorine atom bonded to one of the carbon atoms of a vinyl group; b) if cyclic, $C_nF_aH_bX_c$ where X is a halogen, $a \geq 1$, b=0 to 2n-3, and c=0 to 2n-3, and a+b+c=2n-2, at least one F being bonded to a doubly bonded carbon atom, preferably being a vinyl F. Examples of such fluoroolefins are vinyl fluoride (VF), vinylidene fluoride ($VF_2$), trifluoroethylene, chlorotrifluoroethylene (CTFE), tetrafluoroethylene (TFE), and hexafluoropropylene (HFP).

A subset of the above class of fluoroolefins has the general formula $CF_2=CF-R$. R may be hydrogen, alkyl with or without halogen substitutions and, if so substituted, preferably with chlorine and/or fluorine, preferably fluoroalkyl, and more preferably perfluoroalkyl, and may be linear or branched, or cyclic.

Preferably the fluoroolefin has at least two vinyl fluorine atoms, and more preferably, three. Preferably in the fluoroolefin at least about 35% of the monovalent atoms are fluorine atoms, more preferably at least about 50%, more preferably still at least about 75%, and most preferably the fluoroolefin is a perfluoroolefin. Preferably the fluoroolefin is an alpha-fluoroolefin, that is an olefin in which the double bond is at the end of the olefin molecule. Preferred fluoroolefins are TFE and HFP.

TFE can be safely and conveniently shipped and stored as a mixture with carbon dioxide ($CO_2$), as disclosed in U.S. Pat. No. 5,345,013. It is an advantage of the process according to this invention that the mixture, sometimes called the shipping mixture, can be used without the need for isolating the TFE from $CO_2$.

The term sulfite ($SO_3^=$) is used herein with the understanding that in aqueous solution this species is in equilibrium with bisulfite ($HSO_3^-$). The ratio of sulfite to bisulfite is a function of the pH of the solution. This equilibrium may also include sulfurous acid ($H_2SO_3$) and sulfur dioxide ($SO_2$). $SO_3^=$/$HSO_3^-$ forms a buffer that with proper control can effectively buffer the reaction according to this invention without the introduction of extraneous materials such as borax and phosphate, which can be the source of impurities in the product and, in addition, add to the cost of ingredients, and increase the variety of chemicals in the waste product, thus increasing the difficulty and cost of disposal or recovery.

The optimum pH range for the formation of hydrofluoroalkanesulfonic acids according to this invention is about 4 to 12, preferably about 5 to 11, more preferably about 5 to 10, and most preferably about 5 to 9. Optimum pH can be attained by adding a sulfite source such as sulfur dioxide ($SO_2$), sulfurous acid, bisulfite, and/or sulfite to water, and adjusting the pH by further addition of a reagent that does not introduce extraneous materials into the reaction. By non-extraneous material is meant a material that is related to the necessary ingredients of the reaction according to this invention, these being water, sulfite or sulfurous acid. Ingredients that are fugitive in the sense of being easily removed without contamination of the product or residue, such as carbonate, bicarbonate, and/or carbon dioxide are not considered extraneous materials.

Such non-extraneous materials include hydroxide, carbon dioxide ($CO_2$), bicarbonate, carbonate, sulfuric acid, bisulfate, and sulfate, and sulfurous acid, bisulfite, and sulfite. If the initially made solution has too high a pH, one or more of the acidic types of materials listed above, e.g. $SO_2$, sulfuric acid, bisulfate, or $CO_2$ are added. If the initially made solution has too low a pH, one or more of the basic types of materials listed above, e.g. hydroxide, sulfite, or carbonate, are added.

$CO_2$ is a particularly effective reagent. When present, it acts to buffer the reaction and suppress all but the desired product. It is believed that it does this by reacting, in the form of carbonic acid ($H_2CO_3$) with which it exists in equilibrium in water, with hydroxyl ($OH^-$) ion formed in the reaction of sulfite, the effective reactant, with fluoroolefin, e.g., TFE in equation (2) below:

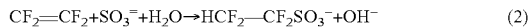
$$CF_2=CF_2+SO_3^=+H_2O \rightarrow HCF_2-CF_2SO_3^-+OH^- \qquad (2)$$

One mole of $H_2CO_3$ reacts with two $OH^-$ to form carbonate ($CO_3^=$), thereby suppressing the reaction of $OH^-$ with TFE to form difluoroacetic acid. Therefore, one mole of $CO_2$ will neutralize $OH^-$ from the reaction of two moles of TFE, or other fluoroolefin with $SO_3^=$. If TFE if supplied in the form of TFE:$CO_2$ shipping mixture, typically about 30/70 mole ratio, it may be used directly, recognizing that $CO_2$ is in excess of the stoichiometric amount for $OH^-$ neutralization. Preferably, the shipping mixture is treated before use, such as by membrane separation, to bring the mole ratio closer to the stoichiometric 66:33 (TFE/$CO_2$), such as in the range about 50:50 to about 75:25, more preferably about 60:40 to 70:30, and most preferably about 64:36 to 68:32.

Alternatively, fluoroolefin and $CO_2$ may be added in separate streams in the desired ratio, or the $CO_2$ addition may be controlled by means that monitor the reaction solution pH and adjust $CO_2$ addition rate to maintain pH in the desired range.

It is preferred that, for reagents that are ionic, those with alkali metal cations be used, preferably the sodium or potassium ion, more preferably the potassium ion. These cations are also referred to herein as counter ions to the hydrofluoroalkanesulfonates.

Contrary to the teaching of the prior art, it is not desirable, let alone beneficial, to have radical initiators, particularly radical initiators capable of initiating the polymerization of fluoroolefins, present in the reaction mixture and preferably no free radical initiator is added. Furthermore, oxygen should preferably be excluded from the reaction vessel, since oxygen is capable of initiating polymerization of fluoroolefins, especially of TFE. When the fluoroolefin to be used in the reaction is TFE, it is particularly important to exclude oxygen or initiators because TFE polymerization proceeds vigorously with substantial generation of heat. For less easily polymerizable fluoroolefins, such as HFP, safety considerations related to oxygen are less critical. However, fluoroolefins are costly and initiators and oxygen cause side reactions that compete with formation of hydrofluoroalkanesulfonic acid, reducing yield and creating useless byproducts that can foul the reactor and cause plugging in lines. In addition, oxygen reacts with sulfite to form sulfate. Since the sulfite concentration is important to controlling the pH of the reaction, such oxidation by oxygen is undesirable.

In the process according to this invention, a suitable vessel, preferably of stainless steel or other corrosion resistant metal, is charged with aqueous sulfite solution. The solution may be prepared outside the vessel, or made in situ, by charging water and dry ingredients. It is preferred that the water be deionized and oxygen-free. If it is desired to avoid handling dry ingredients, the sulfite solution may be prepared by adding sulfur dioxide ($SO_2$) to aqueous caustic, preferably sodium or potassium hydroxide. pH of the solution should be adjusted to about 4-12. If a sulfite salt, such as sodium or potassium sulfite is the sulfite source, sulfuric acid is a convenient acid for pH adjustment.

After the aqueous sulfite is charged, the vessel is cooled to about 0° C. to −40° C., evacuated and then charged with nitrogen or other inert gas at least once and preferably 2 to 3 times to eliminate oxygen, particularly if TFE is to be the fluoroolefin. The vessel is evacuated and then charged with the fluoroolefin, closed, and heating is begun. Temperature is raised to about 125° C. and held there with stirring, shaking, or other means of agitating the vessel contents for about 2 to 12 hours. If the fluoroolefin is a gas, progress of the reaction may be monitored by the drop in pressure as the fluoroolefin is consumed. At the end of the reaction time, the vessel is cooled to room temperature, vented, and the contents discharged.

The aqueous contents are concentrated by removal of water, preferably at reduced pressure, preferably in a rotary evaporator. More preferably, water-removal in the rotary evaporator is not carried to the point of dryness. Rather, water is further removed by freeze drying. Freeze drying results in a finely divided, easily handled, low moisture solid that on treatment with oleum gives yields superior to those obtained from non-freeze dried solids, which tend to be hard and lumpy. The product from the freeze drier preferably contains less than about 5 wt % water, more preferably contains less than about 1 wt % water, and most preferably contains less than about 0.5 wt % water.

Also preferable, is the removal of water by spray-drying the aqueous reaction product.

If the potassium salt of the sulfite reactant is used in reaction with HFP or higher fluoroolefins, it is surprisingly found that, upon cooling after the reaction is ended, the product precipitates in good yield and high purity without further treatment, apart from drying. Thus, in accordance with a preferred form of the invention, conditions are employed which cause the potassium salt to precipitate from solution. Preferably, cooling is to less than about 15° C., more preferably to less than about 10° C., and most preferably to less than about 5° C. Cooling preferably should not be so low as to cause freezing of the reactor contents.

The discovery of the easy recovery in high purity and high yield of the potassium salt of the sulfonate product of the reaction of sulfite with HFP or higher molecular weight fluoroolefin, make the potassium salt a preferred salt in the process according to this patent. In addition, if the sulfonate salt is isolated without conversion to the sulfonic acid, it is a convenient source of anion in the production of ionic liquids and photoacid generators.

The preferred potassium salts of products according to this high purity, high conversion synthesis are those of the general formula $R_f$—CFH—$CF_2SO_3K$, wherein $R_f$ is selected from the group consisting of fluoroalkyl groups, perfluoroalkyl groups, cyclofluoroalkyl groups, and cycloperfluoroalkyl groups, said groups optionally containing ether oxygen.

When the desired final product is the acid, after water-removal, the product is directly treated with oleum. The term "oleum" means sulfuric acid ($H_2SO_4$) containing sulfur trioxide ($SO_3$), preferably in the range of about 1 to 15 wt %. The oleum is preferably used in a weight ratio of at least about 1 part oleum per part dried product. By using oleum, rather than concentrated sulfuric acid, which generally contains from 2-5 wt % water, formation of hydrofluoroalkanesulfonic acid hydrate is avoided. The acid hydrates, for example of TFESA or of the acid derived from HFP, are waxy solids at room temperature. They can solidify in the condenser during distillation unless the temperature of the condenser coolant is controlled, which is a burdensome requirement.

Commercially available oleum may have too high an $SO_3$ content. If so, the $SO_3$ concentration can be reduced by mixing the commercial oleum with sulfuric acid. The sulfuric acid addition dilutes the commercial oleum, and water in the sulfuric acid reacts with some of the $SO_3$ to form sulfuric acid. The result is oleum of lower $SO_3$ concentration.

Addition of the oleum gives a slurry, which, on heating in the still, may form a solution, depending on the particular sulfonic acid.

A large excess of oleum is not desirable. It can lead to reduced yields of the sulfonic acid and formation of lower boiling product, believed to be sulfonic acid ester. In the process there should be a small amount, preferably no more than about 5 wt %, more preferably no more than about 3 wt %, most preferably no more than about 1 wt %, of low boiling material coming off the distillation before the desired sulfonic acid product. This ensures that no hydrate remains to foul the still. Low boiling material in excess of this is an indication that too much oleum is being used, and the amount should be reduced.

The term "directly treating" with oleum means that no intervening extraction steps are used and the oleum is mixed or contacted with the product for treatment. The oleum mixture is then heated to boiling and the product acid distilled off. If the acid is found to be in hydrate form, that is combined with water, stronger oleum or more complete water removal from the product is desirable to avoid additional process steps, such as treatment of the acid hydrate with thionyl chloride to make the unhydrated acid.

The process as described above may be carried out as a batch process. The process according to this invention may also be run continuously, with continuous or periodic drawing off of the liquid contents of the reactor and continuous or periodic replenishment of reactants.

EXAMPLE 1

Example 1, parts A-F, illustrate the steps of a process of the invention with TFE as the fluoroolefin prior to the step of directly treating with oleum to produce the hydrofluoroalkane sulfonic acid. Carrying out the reaction with sulfite at a pH of about 4 to about 12, suppresses the undesirable hydration reaction of the fluoroolefin with its attendant production of a carboxylic acid byproduct, in the case of TFE, difluoroacetic acid. Parts A-C employ a sodium sulfite solution and the pH is adjusted with sulfuric acid. Parts D-F show the effectiveness of $CO_2$, in the absence of any adjustment of pH by acid addition, in preventing significant production of difluoroacetic acid.

Part A

A Hastelloy® C276 vessel (shaker tube) is used. A solution is prepared of sodium sulfite (23.94 g) and deionized water (90 ml) and the pH adjusted to 5.59 with sulfuric acid to give a solution of final volume 130 ml. The solution is loaded into the tube and the tube cooled, evacuated and purged with nitrogen. Following this, tetrafluoroethylene (TFE, 38 g) is loaded to the tube. The starting temperature of the tube is −32.3° C., and the temperature is raised to 125° C. over 2.5 hours. The pressure, during this temperature rise, increases from 182 psig (1360 kPa) to 545 psig (3860 kPa). The temperature of 125° C. is maintained for 12 hours, during which time the pressure drops quickly (within 2 hours) from 545 psig (3760 kPa) to 353 psig (2530 kPa) and then remains approximately constant. The reaction is allowed to cool to room temperature before venting excess gases and rinsing the reaction mixture from the shaker tube with deionized water. The final pH of the reaction mixture is 7.25.

The water is removed from the reaction mixture under reduced pressure in a rotary evaporator to give 51 g of product. A sample of the resulting solid analyzed by $^1$H NMR in $D_2O$ to contain <1% difluoroacetic acid. Fluorine ($^{19}$F) NMR ($D_2O$) δ-122.0 dt, $^3J_{FH}$=6 Hz, $^3J_{FF}$=6 Hz, 2F); −136 (dt, $^2J_{FH}$=53 Hz, 2F), consistent with tetrafluoroethanesulfonate (TFES-Na).

Proton ($^1$H) NMR ($D_2O$) δ 6.4 (tt, $^2J_{FH}$=53 Hz, $^3J_{FH}$=6 Hz, 1H). A portion of the crude sodium tetrafluoroethanesulfonate (TFES-Na) is extracted with four times its weight of acetone, filtered, and the acetone removed in a rotary evaporator. The product contains >99% of (TFES-Na) as shown by NMR and chemical analysis.

Part B

In the same vessel as in Example 1, a solution is prepared of sodium sulfite (23.94 g) and deionized water (90 ml) and the pH adjusted to 5.67 with sulfuric acid to give a solution of final volume 130 ml. The solution is loaded into the shaker tube (detailed above) and the tube cooled, evacuated and purged with nitrogen. Following this, TFE (38 g) is loaded to the tube. The starting temperature of the tube is −22.1° C., and the temperature is raised to 125° C. over 75 minutes. The pressure, during this temperature rise, increases from 205 psig (1515 kPa) to 594 psig (4200 kPa). The temperature of 125° C. is maintained for 3.5 hours, during which time the pressure drops quickly from 594 psig (4200 kPa) to 372 psig (2660 kPa) and then remains constant. The reaction is allowed to cool to room temperature before venting excess gases and rinsing the reaction mixture from the shaker tube with deionized water. The final pH of the reaction mixture is 7.25.

The water is removed from the reaction mixture under reduced pressure in a rotary evaporator to give 49 g of product. A sample of the resulting solid analyzed by $^1$H NMR in $D_2O$ to contain <0.1% difluoroacetic acid. $^{19}$F NMR ($D_2O$) δ-122 dt, $^3J_{FH}$=6 Hz, $^3J_{FF}$=6 Hz, 2F); −136.2 (dt, $^2J_{FH}$=53 Hz, 2F), consistent with tetrafluoroethanesulfonate (TFES-Na).

$^1$H NMR ($D_2O$) δ 6.4 (tt, $^2J_{FH}$=53 Hz, $^3J_{FH}$=6 Hz, 1H).

A portion of the crude sodium tetrafluoroethanesulfonate (TFES-Na) is extracted with four times its weight of acetone, filtered, and the acetone removed in a rotary evaporator. The product contains >99% of (TFES-Na) as shown by NMR and chemical analysis.

Part C

In the same vessel as in Example 1, a solution is prepared of sodium sulfite (12.6 g) and deionized water (100 ml) and the pH adjusted from 10.06 to 5.53 with concentrated sulfuric acid. The solution is loaded into the shaker tube (detailed above) and the tube cooled, evacuated and purged with nitrogen. Following this, TFE (10 g) and carbon dioxide (13.2 g) are loaded to the tube. The starting temperature of the tube is −28.8° C., and the temperature is raised to 125° C. over 75 minutes. The pressure, during this temperature rise, increases from 109 psig (855 kPa) to 369 psig (2650 kPa). The temperature of 125° C. is maintained for 12.5 hours, during which time the pressure drops steadily from 369 psig (2550 kPa) to 272 psig (1875 kPa). The reaction is allowed to cool to room temperature before venting excess gases and rinsing the reaction mixture from the shaker tube with deionized water. The final pH of the reaction mixture is 6.19.

The water is removed from the reaction mixture under reduced pressure in a rotary evaporator to give 20.3 g of product. A sample of the resulting solid analyzed by $^1$H NMR in $D_2O$ to contain <0.1% difluoroacetic acid. $^{19}$F NMR ($D_2O$) δ-121.9 dt, $^3J_{FH}$=6 Hz, $^3J_{FF}$=6 Hz, 2F); −136.2 (dt, $^2J_{FH}$=53 Hz, 2F), consistent with tetrafluoroethanesulfonate (TFES-Na).

$^1$H NMR ($D_2O$) δ 6.4 (tt, $^2J_{FH}$=53 Hz, $^3J_{FH}$=6 Hz, 1H).

A portion of the crude sodium tetrafluoroethanesulfonate (TFES-Na) is extracted with four times its weight of acetone, filtered, and the acetone removed in a rotary evaporator. The product contains >99% of (TFES-Na) shown by NMR and chemical analysis This Example shows that the reaction proceeds well in the presence of $CO_2$.

Part D

Using the same vessel as in Example 1, sodium sulfite (6.3 g) and water (100 g) are loaded into the shaker tube (detailed above) and the tube cooled, evacuated and purged with nitrogen. Following this, TFE (10 g) and carbon dioxide (22 g) are loaded to the tube. The starting temperature of the tube is −19.4° C., and the temperature is raised to 125° C. over 75 minutes. The pressure, during this temperature rise, increases from 277 psig (1210 kPa) to 833 psig (5850 kPa). The temperature of 125° C. is maintained for 5 hours, during which time the pressure drops steadily from 833 psig (5850 kPa) to 770 psig (5410 kPa). Following a power outage, the temperature is raised back to 125° C. from 110° C. and maintained for four hours, during which time the pressure is constant. The reaction is allowed to cool to room temperature before venting excess gases and rinsing the reaction mixture from the shaker tube with deionized water. The final pH of the reaction mixture is about 8. The water is removed from the mixture under reduced pressure and a sample of the resulting solid analyzed by proton NMR in $D_2O$ to contain <0.1% difluoroacetic acid.

Part E

Using the same vessel as in Example 1, sodium sulfite (12.6 g) and water (100 g) are loaded into the shaker tube (detailed above) and the tube cooled, evacuated and purged with nitrogen. Following this, a pre-combined mixture of TFE (10 g) and carbon dioxide (13 g) (23 g total) are loaded to the tube. The starting temperature of the tube is −20° C., and the temperature is raised to 125° C. over 60 minutes. The pressure, during this temperature rise, increases from 274 psig (1990 kPa) to 598 psig (4125 kPa). The temperature of 125° C. is maintained for 12 hours, during which time the pressure drops steadily from 598 psig (4225 kPa) to 554 psig (3920 kPa). The reaction is allowed to cool to room temperature before venting excess gases and rinsing the reaction mixture from the shaker tube with deionized water. The final pH of the reaction mixture is between 7 and 8. A sample of the solution is diluted in $D_2O$ and analyzed by 1H NMR to contain <0.1% difluoroacetic acid.

Part F

A 1-liter Hastelloy C276 stirred reaction vessel is charged with a solution of 53 g anhydrous sodium sulfite ($Na_2SO_3$, 98%, Acros, 0.42 mol) and 300 ml of deionized water. The pH of this solution is 10.3. The vessel is held at 25° C., evacuated to atmospheric pressure, and purged with nitrogen. The evacuate/purge cycle is repeated four more times. To the vessel is then added 450 psig (3.2 MPa) of a 26/74 mol % mixture of tetrafluoroethylene and carbon dioxide (approximately 36 g TFE). The vessel is heated to 125° C. with agitator speed of 1000 rpm at which time the inside pressure is 650 psig (4.60 MPa). The reaction is allowed to proceed at this temperature for 4 hr during which time the pressure drops to 440 psig (3.14 MPa). The vessel is vented and cooled to 25° C. The pH of the colorless reaction solution is 8.0 which shows that dissolved carbon dioxide in the form of carbonic acid is indeed functioning as a buffer.

The water is removed in vacuo on a rotary evaporator to produce a wet solid. The solid is then placed in a vacuum oven (120° C., 80 Torr) for 4 hr to reduce the water content to approximately 0.9 wt.% (82 g crude material). The crude TFES-Na is purified and isolated by extraction with 800 ml reagent grade acetone, filtration, and drying to give 57 g of product.

19F NMR ($D_2O$) δ-121.8 dt, $^3J_{FH}$=6 Hz, $^3J_{FF}$=6 Hz, 2F); −135.9 (dt, $^2J_{FH}$=53 Hz, 2F).

1H NMR ($D_2O$) δ6.4 (tt, $^2J_{FH}$=53 Hz, $^3J_{FH}$=6 Hz, 1H).

% Water by Karl-Fisher titration: 0.9 wt. %.

Melting point (DSC) 298° C.

TGA (air): 10% wt. loss at 382° C., 50% wt. loss at 424° C.

TGA (nitrogen): 10% wt. loss at 377° C., 50% wt. loss at 431° C.

EXAMPLE 2

Example 2 illustrates the reaction of TFE in a process of the invention. A 1-gallon Hastelloy® C276 reaction vessel is charged with a solution of 176 g potassium bisulfite hydrate ($KHSO_3.H2O$, 95%, Aldrich, 1.0 mol), 610 g potassium metabisulfite ($K_2S_2O_5$, 99%, Mallinckrodt, 2.8 mol) and 2000 ml of deionized water. The pH of this solution is 5.8. The vessel is cooled to 18° C., evacuated to −3 psig (80 kPa), and purged with nitrogen. The evacuate/purge cycle is repeated two more times. To the vessel is then added 66 g tetrafluoroethylene (TFE) and it is heated to 100° C. at which time the inside pressure is 150 psig (1.14 MPa). The reaction temperature is increased to 125° C. and kept there for 3 hr. As the TFE pressure decreases due to the reaction, more TFE is added in small aliquots (20-30 g each) to maintain operating pressure roughly between 150 and 200 psig (1.14 and 1.48 MPa). Once 500 g (5.0 mol) of TFE has been fed after the initial 66 g precharge, the vessel is vented and cooled to 25° C. The pH of the clear light yellow reaction solution is 10-11. This solution is buffered to pH 7 through the addition of 16 g of potassium metabisulfite before workup.

The water is removed in vacuo on a rotary evaporator to produce a wet solid. The solid is then placed in a freeze dryer (Virtis Freezemobile 35×1) for 72 hr to reduce the water content to approximately 1.5 wt % (1387 g crude material). The theoretical mass of total solids is 1351 g. The mass balance is very close to ideal. The isolated solid has slightly higher mass due to moisture. This added freeze drying step has the advantage of producing a free-flowing white powder whereas treatment in a vacuum oven results in a soapy solid cake that is difficult to remove. It has to be chipped and broken out of the flask.

A portion of the crude potassium tetrafluoroethanesulfonate (TFES-K) is further purified and isolated by extraction with reagent grade acetone, filtration, and drying. Analysis give the following results:

$^{19}$F NMR (D$_2$O) δ-122.0 dt, $^3J_{FH}$=6 Hz, $^3J_{FF}$=6 Hz, 2F); −136.1 (dt, $^2J_{FH}$=53 Hz, 2F).

$^1$H NMR (D$_2$O) δ 6.4 (tt, $^2J_{FH}$=53 Hz, $^3J_{FH}$=6 Hz, 1H).

% Water by Karl-Fisher titration: 580 ppm.

Analysis calculated for C$_2$HO$_3$F$_4$SK: C, 10.9; H, 0.5; N, 0.0 Found: C, 11.1; H, 0.7; N, 0.2.

Melting point by differential scanning calorimeter (DSC) 242° C.

Thermal gravimetric analysis (TGA) (air): 10% wt. loss at 367° C., 50% wt. loss at 375° C. TGA (nitrogen): 10% wt. loss at 363° C., 50% wt. loss at 375° C.

A 100 ml round bottom flask with a sidearm is equipped with a digital thermometer and a magnetic stirbar and placed in an ice bath under positive nitrogen pressure. To the flask is added 50 g crude TFES-K from the previous step along with 30 g of concentrated sulfuric acid (EM Science, 95-98%) and 78 g oleum (Acros, 20 wt % SO$_3$) while stirring. This amount of oleum is chosen so that the SO$_3$ reacts with and removes the water in the sulfuric acid as well as in the crude TFES-K while still being present in slight excess. The mixing causes a small exotherm which is controlled by the ice bath. Once the exotherm is over, a distillation head with a water condenser is placed on the flask and it is heated under nitrogen behind a safety shield. The pressure is slowly reduced using a PTFE membrane vacuum pump (Buchi V-500) in steps of 100 Torr (13 kPa) in order to avoid foaming. A dry-ice trap is also placed between the distillation apparatus and the pump to collect any excess SO$_3$. Once the pot temperature reaches 120° C. and the pressure is held at 20-30 Torr (2.7-4.0 kPa) a colorless liquid starts to reflux and later distills at 110° C. and 31 Torr (4.1 kPa). A forerun of lower-boiling impurity (2.0 g) is obtained before collecting 28 g of the desired colorless acid, TFESA.

In the 50 g of impure TFES-K, it is calculated that approx. 39.8 g TFES-K is present. Thus, the 28 g of product is an 85% yield of TFESA from TFES-K as well as an 85% overall yield from TFE. Analysis gives the following results: $^{19}$F NMR (CD$_3$OD) δ-125.2 dt, $^3J_{FH}$=6 Hz, $^3J_{FF}$=8 Hz, 2F); −137.6 (dt, $^2J_{FH}$=53 Hz, 2F). $^1$H NMR (CD$_3$OD) δ 6.3 (tt, $^3J_{FH}$=6 Hz, $^2J_{FH}$=53 Hz, 1H).

EXAMPLE 3

This example demonstrates the reaction of hexafluoropropylene (HFP) according to this invention. A 1-gallon Hastelloy® C276 reaction vessel is charged with a solution of 25 g anhydrous sodium sulfite (Na$_2$SO$_3$, 98%, Acros, 0.20 mol), 73 g sodium bisulfite (NaHSO$_3$, Aldrich, 0.70 mol) and 400 ml of deionized water. The pH of this solution is 5.7. The vessel is cooled to 4° C., evacuated to −3 psig (80.6 kPa), and then charged with 120 g of hexafluoropropylene (HFP, 0.8 mol, 48 psig (430 kPa)). The vessel is heated with agitation to 120° C. and kept there for 3 hr. The pressure rises to a maximum of 250 psig (1825 kPa) and then drops down to 25 psig (275 kPa) within 30 minutes. At the end, the vessel is cooled and the remaining HFP is vented and the reactor is purged with nitrogen. The final solution has a pH of 7.3.

The water is removed in vacuo on a rotary evaporator to produce a wet solid. The solid is then placed in a vacuum oven (150 Torr (20 kPa), 140° C., 48 hr) to produce 219 g of white solid which contained approximately 1 wt % water. The theoretical mass of total solids is 217 g.

A 100 ml round bottom flask with a sidearm is equipped with a digital thermometer and a magnetic stirbar and placed in an ice bath under positive nitrogen pressure. To the flask is added 50 g crude sodium hexafluoropropanesulfonate (HFPS-Na) from the previous step along with 30 g of concentrated sulfuric acid (EM Science, 95-98%) and 58.5 g oleum (Acros, 20 wt % SO$_3$) while stirring.

This amount of oleum is chosen so that the SO$_3$ will react with and remove the water in the sulfuric acid as well as in the crude HFPS-Na while still being present in slight excess. The mixing causes a small exotherm which is controlled by the ice bath. Once the exotherm is over, a distillation head with a water condenser is placed on the flask, which is heated under nitrogen behind a safety shield. The pressure is slowly reduced using a PTFE membrane vacuum pump (Buchi V-500) in steps of 100 Torr (13 kPa) to avoid foaming. A dry-ice trap is also placed between the distillation apparatus and the pump to collect any excess SO$_3$. When the pot temperature reaches 100° C. and the pressure is held at 20-30 Torr (2.7-4 kPa) a colorless liquid started to reflux and later distilled at 118° C. and 23 Torr (3.1 kPa). A forerun of lower-boiling impurity (1.5 g) is obtained before collecting 36.0 g of the desired acid, hexafluoropropanesulfonic acid (HFPS).

In the 50 g of impure HFPS-Na, it is calculated that approx. 44 g HFPS-Na is present. Thus, the 36.0 g of HFPS product is an 89% yield from HFPS-Na as well as an 84% overall yield from HFP.

The crude HFPS-Na from the vacuum oven drying step is further purified and isolated by extraction with reagent grade acetone, filtration, and drying.

$^{19}$F NMR (D$_2$O) δ-74.5 m, 3F); −113.1, −120.4 (ABq, J=264 Hz, 2F); −211.6 (dm, 1F).

$^1$H NMR (D$_2$O) δ5.8 (dm, $^2J_{FH}$=43 Hz, 1H).

Melting point (DSC) 126° C.

TGA (air): 10% wt. Loss at 326° C., 50% weight loss at 446° C.

TGA (N$_2$): 10% wt. loss at 322° C., 50% weight loss at 449° C.

EXAMPLE 4

Synthesis of Potassium
1,1,2,3,3,3-Hexafluoropropanesulfonate (HFPS-K)

This example demonstrates the surprising superiority of the synthesis using the potassium salt of the sulfite reactants to make the potassium salt of 1,1,2,3,3,3-hexafluoropropanesulfonate in high purity and good yield without special separation and purification steps.

A 1-gallon Hastelloy C276 reaction vessel is charged with a solution of 130 g (0.74 mol) potassium sulfite hydrate (K2SO3.xH2O, 95%, Aldrich), 448 g (2.02 mol) potassium metabisulfite (K2S2O5, 99%, Mallinckrodt) and 1300 mL of deionized water. The pH of this solution is 6.1. The vessel is cooled to −35° C., evacuated to −3 psig (83 kPa), and purged with nitrogen. The evacuate/purge cycle is repeated two more times. To the vessel is then added 550 g (3.67 mol) hexafluoropropylene (HFP) and it is heated to 125° C. During heating, the internal pressure increased to a maximum of 320 psig (2.3 MPa) at 80° C., then rapidly dropped to 23 psig (260 kPa) within the next 20 min. The total reaction time from the start of heating is 75 min. The vessel is then vented and cooled to 25° C.

The reaction product is a white precipitate in a mother liquor of pH 7.0. The crude reaction mixture is cooled to 5° C. and vacuum filtered to isolate the solid product which is further dried in vacuo (70° C., 40 Torr (5 kPa), 48 hr) to afford 788 g (2.92 mol) of white powdered product (80% yield).

Water by Karl-Fisher titration: 0.15 wt %.

Analysis Calculated for $C_3HO_4SF_6$: C, 13.3; H, 0.4; N, 0.0.

Found: C, 13.5; H, 0.4; N, 0.1.

It is seen that the product precipitates in 80% yield and high purity on cooling of the reaction mixture. This is unlike the behavior of the sodium salt in Example 3, where the cooled reaction mixture is a solution without significant precipitate, and in which evaporation is necessary to recover the salt, which then requires further purification.

EXAMPLE 5

Synthesis of Potassium 1,1,2,3,3,3-Hexafluoropropanesulfonate (HFPS-K)

Example 4 is repeated except that the amount of water is reduced to 1000 ml. The product precipitates in 85% yield and the same high purity found in Example 4.

What is claimed is:

1. Process for manufacture of potassium hydrofluoroalkanesulfonate with at least one hydrogen bonded to a carbon atom adjacent to the carbon atom bonded to the sulfonate group comprising:
   a) contacting fluoroolefin having at least three carbon atoms with an aqueous solution of sulfite and counter ion in which the counter ion comprises potassium, said solution having a pH of about 4 to 12;
   b) employing conditions which cause potassium hydrofluoroalkanesulfonate to precipitate from said solution.

2. The process of claim 1 wherein said employing conditions which cause potassium hydrofluoroalkanesulfonate to precipitate from said solution comprise cooling.

* * * * *